(12) United States Patent
Sato et al.

(10) Patent No.: US 9,796,092 B2
(45) Date of Patent: Oct. 24, 2017

(54) MULTI-ARTICULATED MANIPULATOR

(71) Applicant: NIPPON THOMPSON CO., LTD., Tokyo (JP)

(72) Inventors: Takashi Sato, Mino (JP); Tetsuya Sakai, Mino (JP)

(73) Assignee: NIPPON THOMPSON CO., LTD., Tokyo (JP)

(*) Notice: Subject to any disclaimer, the term of this patent is extended or adjusted under 35 U.S.C. 154(b) by 0 days.

(21) Appl. No.: 15/002,568

(22) Filed: Feb. 9, 2016

(65) Prior Publication Data

US 2016/0207206 A1 Jul. 21, 2016

(30) Foreign Application Priority Data

Jan. 21, 2015 (JP) ................... 2015-009257

(51) Int. Cl.
| | |
|---|---|
| *A61B 34/30* | (2016.01) |
| *B25J 9/16* | (2006.01) |
| *B25J 9/06* | (2006.01) |
| *B25J 9/10* | (2006.01) |
| *B25J 15/02* | (2006.01) |
| *B25J 17/02* | (2006.01) |

(52) U.S. Cl.
CPC ............ *B25J 9/1689* (2013.01); *A61B 34/30* (2016.02); *B25J 9/065* (2013.01); *B25J 9/106* (2013.01); *B25J 15/022* (2013.01); *B25J 17/0275* (2013.01); *A61B 2034/301* (2016.02); *A61B 2034/305* (2016.02); *Y10S 901/28* (2013.01)

(58) Field of Classification Search
CPC .............. A61B 34/30; A61B 2034/301; A61B 2034/305; B25J 9/065; B25J 9/106; B25J 15/002; B25J 17/0275
See application file for complete search history.

(56) References Cited

U.S. PATENT DOCUMENTS

| | | | |
|---|---|---|---|
| 4,848,179 A * | 7/1989 | Ubhayakar | ................ B25J 9/06 74/490.04 |
| 2004/0193146 A1* | 9/2004 | Lee | ...................... A61B 17/062 606/1 |

FOREIGN PATENT DOCUMENTS

| | | |
|---|---|---|
| JP | 2005169011 A | 6/2005 |
| JP | 2007292276 A | 11/2007 |
| JP | 2011083476 A | 4/2011 |

(Continued)

*Primary Examiner* — Gerald McClain
*Assistant Examiner* — Ronald Jarrett
(74) *Attorney, Agent, or Firm* — Browdy and Neimark, PLLC (57) ABSTRACT

This multi-articulated manipulator is rich in reliability and follow-up property in medical applications. The multi-articulated manipulator is composed of more than one hollow outer shell, joint members to connect the outer shells each other, a grasping member fastened for rocking movement to the foremost outer shell, and a power transmission shaft to actuate the grasping member and the outer shell in a bending manner independently from each other. The power transmission shaft is composed of a universal join allowed to bend independently from each other and transmit the rotating torque, and a transmission shaft capable of making expansion and shrinkage and able to transmit rotating torque. The power transmission shaft at the foremost end thereof has male threads mating with the nut made at the boss portion inside the outer shell.

16 Claims, 10 Drawing Sheets

(56) References Cited

FOREIGN PATENT DOCUMENTS

JP            4984280     *  7/2012  ............. B25J 17/00
JP       2013252338  A    12/2013

* cited by examiner

MULTI-ARTICULATED MANIPULATOR

FIELD OF THE INVENTION

The present invention relates to a manipulator or a forceps having more than one articulation, which is adapted for a variety of instruments applied to for example medical robots, medical instruments, manipulators and the like.

BACKGROUND OF THE INVENTION

A driving mechanism for surgical is disclosed in, for example, Published Unexamined Patent Application in Japan No. 2007-292 276, which is energized with an input of rotation to make a bending and/or curvature. With the driving mechanism as cited earlier, the manipulator has a bending link to join connecting members together and grasping links. The grasping links are connected to the connecting members against axial direction. The grasping links each have a first shaft and a second shaft, the first shaft having second male threads mating with a second plate of the connecting member and the second shaft having first male threads mating with a first plate of the connecting member. The first and second male threads are made inversely each other with the same pitch. With the relation of the male threads around the shafts, the connecting members moves to approach each other when the bending link is rotated in any one direction, whereas the connecting members moves away from each other when the bending link is rotated in opposite direction.

Moreover, a multi-freedom manipulator is disclosed in, for example, Published Unexamined Patent Application in Japan No. 2005-169 011, which is superior durability and accuracy in control, and further easier in attaching and/or detachability to the sterilizers, washers and driving means. The multi-freedom manipulator has at least three freedom of relative opening/closing movement of a pair of grasping members, rotation of grasping members around a first axis, and rotation of the grasping members around a second axis lying on an imaginary plane perpendicular to the first axis. With the multi-freedom manipulator constructed as stated earlier, the power applied from the actuator is converted through first-three link mechanisms into relative opening/closing movement of the grasping members, rotating movement around a first axis and rotating movement around a second axis.

With the medical manipulator, moreover, the working parts on the foremost ends of the forceps are actuated with wires for power transmission. In Published Unexamined Patent Application in Japan No. 2011-083 476, there is disclosed a medical manipulator in which the forceps is operated without urging the wire against one of the arms of the forceps. The medical forceps usually has a pair of operable arms, operating means allowing any one of first pulling wire and second pulling wire to pull towards a base end while another pulling wire is pulled towards a foremost end, a power transmission mechanism among the arms and the operating means. With the power transmission mechanism constructed as stated earlier, a pair of pulling wires and a pair of second wires are connected each other through a pair of opening/closing members. Thus, just as the first pulling wire is pulled towards the base end thereof, the second pulling wire is pulled towards the foremost end thereof and the opening/closing members are moved towards closing phase. Further, just as the second pulling wire is pulled towards the base end thereof, the first pulling wire is pulled towards the foremost end thereof and the opening/closing members are moved towards opening phase.

Disclosed in, for example, Published Unexamined Patent Application in Japan No. 2013-252 338, there is disclosed a medical treatment member which has a first bending tubular member lying on a foremost end side, a first wire member whose one end is fixed to the foremost end of the first tubular member and another end is disposed for rotation on a based end of the first tubular member and a driving mechanism is provided to rotate another end of the first wire member. The first wire member causes a twisted condition owing to the rotation of another end of the first wire member, thereby generating the stress in the shrinkage direction between the opposite ends of the first wire member to get the first tubular member bending.

In conventional forceps in which the working ends on the forceps are mainly actuated through the power transmission of wires, there has been problems to be solved in the follow-up and response involved with time lag caused by variation in tension of the wire which is subject to expansion and contraction. As a result, the wire has come to rupture or cutting to lose the accurate operation and the certain power transmission. With the conventional forceps, moreover, the rotation of the connecting part is inputted to get the connecting part to bend or curve. However, as the driving part as a whole is driven to bend by the combination of a limiting universal joint with a driving universal joint, the forceps constructed as stated earlier can't be bent independently at every joint and therefore unsuited for subtle operation. In the conventional multi-freedom manipulators in which the linkage part is actuated with the back-and-forth motion transmitted from the actuator to drive the linkage part to make the joints the 2-axes movement of up-and-down and right-and-left, they are unsuited to make small movements every joint. In the conventional multi-freedom manipulators constructed as stated earlier, there is a shortcoming of less rigidity because of slender and long linkage part.

SUMMARY OF THE INVENTION

The present invention has for its primary object to resolve the major problems as stated earlier, and to provide particularly a manipulator of multi-articulated construction suitable for medical instruments, which comprises more than one hollow outer shells lying lengthwise in series, a joint fastened to opposite ends of the foremost outer shell, grasping members mounted on the foremost outer shell to grasp other objects, joint members to connect the opposed outer shells, and power transmission shafts connected to the outer shells to make it possible to bent independently the outer shells through the joints. The outer shells are made of metallic material to make sure of sufficient rigidity. The power transmission shaft is subject to less tensile variation to improve the response or follow-up property of every joint member after the power transmission shaft has been actuated. The grasping members mounted on the foremost outer shell are finely operated with accuracy at any desired attitude and especially preferable to the medical instruments.

The present invention relates to a multi-articulated manipulator comprising: more than one hollow outer shells lying lengthwise, a joint fastened to opposite ends of the outer shell, a joint member to connect joints opposed to each other, grasping member connected for rotation to the joint members opposed each other, and more than one power transmission shafts which are installed in the outer shell and the joint for expansion and shrinkage and further bending to operate the grasping member and the outer shell independently from each other in a bending manner. The power transmission shafts each have a plurality of transmission shafts capable of extension and shrinkage and transferring a rotating torque, and more than one universal joint capable of bending to connect the adjacent power transmission shafts each other and transmit the rotating torque. The power transmission shaft has second threaded portions which are allowed to mate into first threaded portions made in boss portions in the outer shells.

The outer shell is composed of a first outer shell lying at a foremost end of the outer shell, a second outer shell adjacent to the first outer shell, a third outer shell adjacent to the second outer shell, and a fourth outer shell adjacent to the third outer shell. With the multi-articulated manipulator constructed as stated earlier, the joints fastened to the opposite ends of the outer shell is each composed of the circular part fastened to the outer shell, and a pair of raised portions or U-shaped raised portions extended integrally from circumferentially opposite locations of the circular part.

With the multi-articulated manipulator constructed as stated earlier, moreover, the joint members fastened to the opposite ends of the outer shell are each composed of a circular part fastened to the outer shell, and a pair of raised portions or U-shaped raised portions extended integrally from circumferentially opposite locations of the circular part.

With the multi-articulated manipulator constructed as stated earlier, moreover, the first threaded portion made on the boss portion of the outer shell is a nut, and the second threaded portion made on the transmission shaft portion of the power transmission shaft is the male threads mating with the nut.

The joint is composed of a first joint member to move the grasping member with respect to the outer shell in a vertical direction, a second joint to move the outer shell with respect to the second outer shell in a horizontal direction perpendicular to the vertical direction, a third joint to move the second outer shell with respect to the third shell in a vertical direction and a fourth joint to move the third outer shell relative to the fourth outer shell.

The power transmission shaft is composed of a pair of first power transmission shafts to actuate the grasping member 4 with respect to the first outer shell in a vertical direction, a pair of second power transmission shafts to actuate the first outer shell relative to the second outer shell in a horizontal direction perpendicular to the vertical direction, a single third power transmission shaft to actuate the second outer shell with respect to the third outer shell in a vertical direction, and a single fourth power transmission shaft to actuate the third outer shell with respect to the fourth outer shell in a vertical direction.

The transmission shaft of the power transmission shaft is composed of an operating shaft lying at base end and having a first shaft part, a first folder fitting over the first shaft part in a sliding manner and having fastened to a universal joint, a second folder having a second shaft fit into the first folder for sliding movement, a universal joint having a third shaft fit into the second folder for sliding movement, a driving shaft formed with a male threads and having a fourth shaft which fits for sliding movement into the first folder fastened to the foremost universal joint, and springs installed between the first folder and the operating shaft, and the first folder and the second folder, the second folder and the universal joint, and the first folder and the driving shaft, and pins are diametrically fastened to the first, second, third and fourth shaft parts to fit into slits in the first folder and the second folder to be guided in a lengthwise direction, but kept against rotation.

The transmission shaft of the power transmission shaft is composed of an operating shaft lying at base end and having a first shaft part, a first folder fitting over the first shaft part in a sliding manner and having fastened to a universal joint, a driving shaft formed with a second threads and having a fifth shaft part which fits for sliding movement into the first folder fastened to the foremost universal joint, and springs installed between the operating shaft and the first folder, and the first folder and the driving shaft, and pins fastened diametrically to the first shaft part and the fifth shaft part so as to fit into the slits in the first folder, thereby being guided lengthwise with no rotation.

The universal joint in the power transmission shaft is composed of a pair of lengthwise opposed end yokes, and a middle yoke coupled at the opposite ends thereof with the end yokes by means of joint pins using the universal joints using cross-spider. Moreover, a thin plate fastened inside the outer shell makes engagement with the transmission shaft part of the power transmission shaft to restrict an expansion/shrinkage range of the power transmission shaft. The grasping member is composed of a pair of fingers which are supported for swinging movement each other with connecting pins fastened to the end of the first outer shell, so that the grasping members are operated by the two first power transmission shafts to grasp the object. With the multi-articulated manipulator of the present invention, the outer shell, joint members and transmission shaft are made of metallic material rich in rigidity or stiffness.

Effect of the Invention

The multi-articulated manipulator of the present invention as described above is constituted with more than one outer shell, a grasping member fastened to the foremost outer shell, more than one power transmission shaft to actuate the outer shell in a bending manner and the fingers of the grasping members for opening and closing movement, more than one universal joint allowed to bend independently from each other and transmit the rotating torque, and a transmission shaft capable of making expansion and shrinkage and able to transmit rotating torque. Thus, the multi-articulated manipulator of the present invention causes no expansion and shrinkage due to the tensile force in the power transmission shaft. The transmission shafts are allowed to realize at every outer shell the fine movement independently of every outer shell. The rotating movement of the power transmitting shaft gets the outer shell and the grasping member making bending operation of the outer shell and the grasping members independently of each other with rich following property so as to move to preselected locations and make preparations of preselected attitudes.

With the multi-articulated manipulator of the present invention, as the male threads on the foremost end of the power transmission shaft mate with the nut on the boss portion of the outer shell, rotation of the preselected power transmission shaft connected with the desired outer shell makes the power transmission shaft pull and retract the power transmission shaft to bend immediately the desired outer shell. Moreover, the multi-articulated manipulator of the present invention is rich in reliability operation and better in accurate movement of the grasping members towards the predetermined bending locations. The multi-articulated manipulator of the present invention realizes preferable movement in especially, medical manipulator.

DETAILED DESCRIPTION OF THE INVENTION

The manipulator or forceps having more than one articulation of the present invention is adapted for a variety of instruments applied to for example medical robots, medical instruments, manipulators and the like. The manipulator or forceps having more than one articulation of the present invention will be explained in detail with reference to the accompanying drawings.

Figure 1:
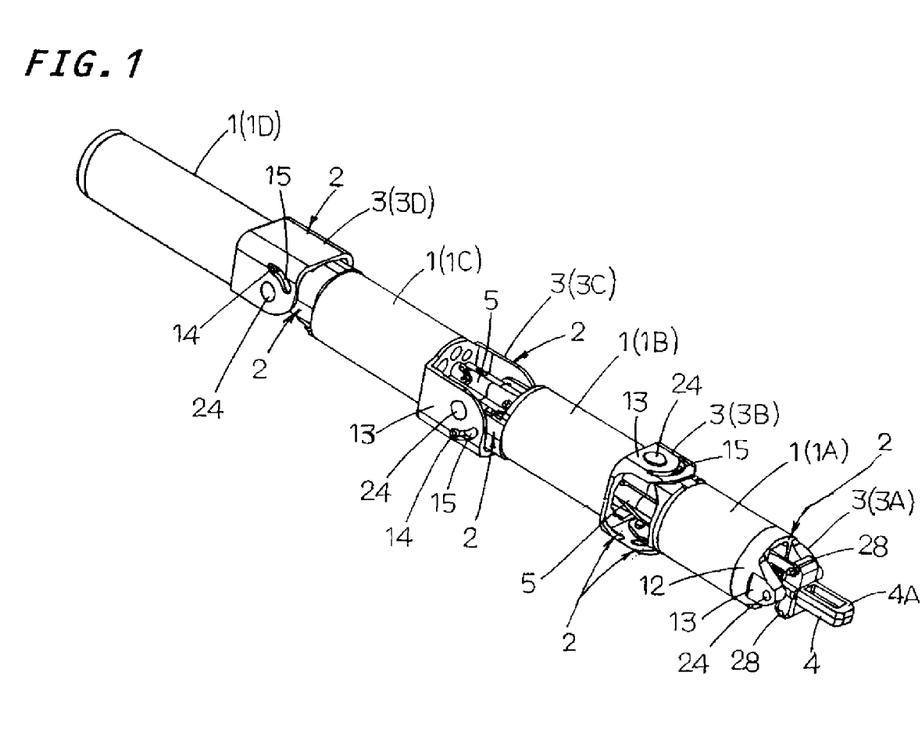
FIG. 1 is a perspective view showing a preferred embodiment of a multi-articulated manipulator according to the present invention.
Figure 2:
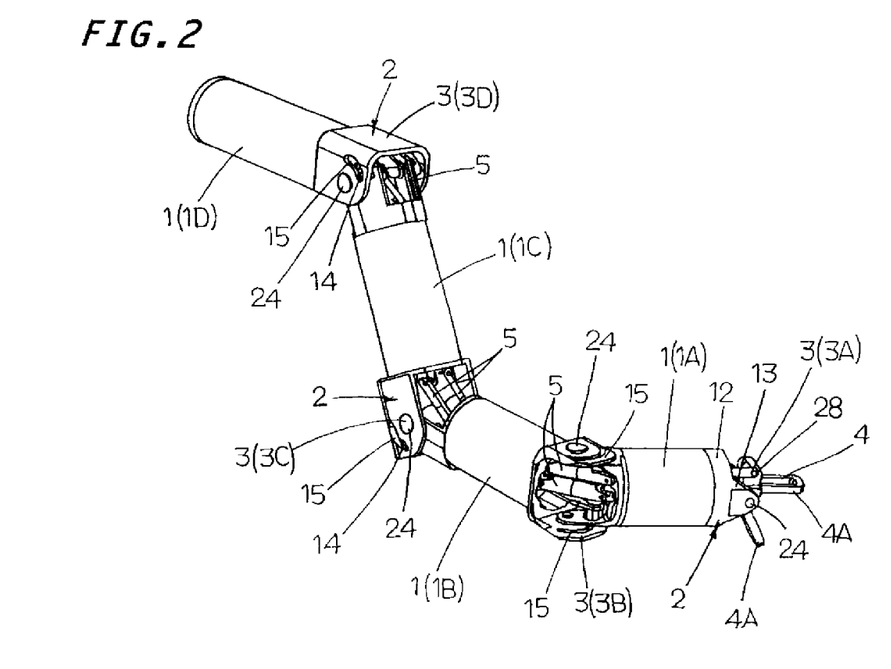
FIG. 2 is a perspective view showing the multi-articulated manipulator of FIG. 1, which is illustrated in bent phase thereof.
Figure 3:
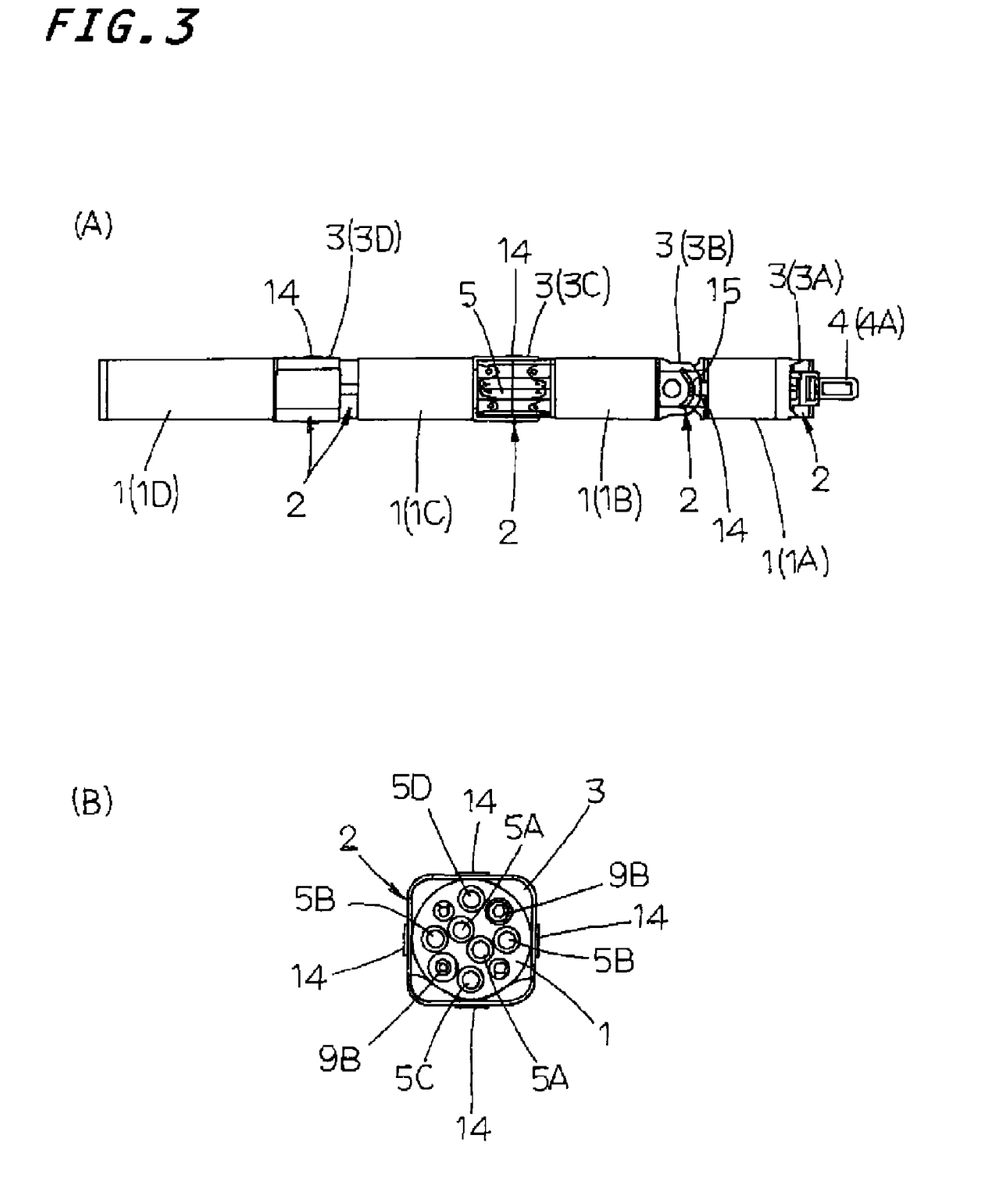
FIG. 3 is a scale-down view of the multi-articulated manipulator of FIG. 1, in which (A) shows a plane view and (B) is an end view.

The manipulator or forceps having more than one articulation of the present invention, as shown in FIGS. 1 to 3, includes more than one hollow outer shells 1 made of metallic material and arranged in series to extend lengthwise direction, metallic joints 2 fastened to opposite ends of every outer shell 1, joint members 3 to couple together adjacent outer shells 1 each other by means of pins 24 in a rocking manner, a grasping member 4 to hold other member or object pivoted to the foremost outer shell 1, and more than one power transmission shaft 5 which fit into the grasping member 4 and the outer shells 1 to make expansion, contraction and folding to actuate the grasping member 4 and outer shell 1 in a foldable manner independently from each other. The power transmission shaft 5 is constituted with more than one universal joint 6 located at a position corresponding to the joint 2, and a metallic transmission shaft 7 able to make expansion and contraction and further transmit the torque. Each outer shell 1 has a boss portion 9 held with a fastening screw 9B to extend out of an inside circumference of the outer shell 1. A nut 10 (first screw) is fastened to the boss portion 9. The foremost end 8 in the transmission shaft 7 has male threads (second threads) 11 fit into the nut 10. The joint members 3 is constituted by the joints 2 which are coupled with pins 24 in a rocking manner, the joints 2 being fastened to opposite ends of the outer shell 1. A thin plate 17 to restrict the movement of the power transmission shaft 5 fits into a groove 19 (refer to FIG. 9) cut in the boss portion 9 of the outer shell 1. The thin plate 17 is fastened to the outer shell 1.

The outer shell 1 is composed of a first outer shell 1A lying at the foremost end of the outer shell 1, a second outer shell 1B adjacent to the first outer shell 1A, a third outer shell 1C adjacent to the second outer shell 1B, and a fourth outer shell 1D adjacent to the third outer shell 1C. Moreover, the joints 2 fastened to the opposite ends of the outer shell 1 is each composed of a circular part 12 fastened to the outer shell 1, and a pair of raised portions 13 or U-shaped raised portions 13 extended integrally from circumferentially opposite locations of the circular part 12. Particularly, the outer shells 1C and 1D each has the U-shaped raised portions 13. The opposed joints 2 of the adjacent outer shells 1 are designed to fit each other. More especially, the raised portion 13 has a hole which allows a pin 24 extend through there. After the opposed joints 2 of the adjacent outer shells 1 fit each other to keep the holes in alignment with each other, a pin 24 fits into the aligned holes to join the adjacent joints 2 to connect the outer shells 1 for relative rotating movement to allow the adjacent outer shells 1 to bend relatively each other. With the multi-articulated manipulator of the present invention, moreover, the joint 2 fastened to one of the opposite ends of the outer shell 1 has a stopper pin 14 extended outwardly and another joint 2 fastened to another of the opposite ends of the outer shell 1 has a curved slit 15. The stopper pin 14 made on the joint 2 makes engagement with the curved slit 15 in the adjacent joints 2 to move along the curved slit 15. The area the adjacent joints 2 are allowed to bend relatively each other is defined with the size of the curved slit 15 in the adjacent joint 2.

Moreover, a nut 10 in the boss portion 9 in the outer shell 1 mates with the male threads 11 on the transmission shaft 7 made at the foremost end of the power transmission shaft 5. Thus, the power transmission shaft 5 as driven to rotate is moved along the nut 10. Each of the outer shells 1A~1D is actuated to make bending movement according to the rotational movement of the corresponding power transmission shaft 5A~5D. The stopper pin 14 is made nearer the foremost end than the pin 24 which connects the joints 2 each other for rocking movement. As a result, the outer shell 1 is allowed to make bending movement in response to back-and-forth movement of the power transmission shaft 5. The joint 2 is allowed to make rocking movement around the pin 24. Namely, the nut 10 is rotated along the male threads 11 according to the rotational movement of the power transmission shaft 5. Then, the rotational movement of the male threads 11 is converted so as to move linearly the nut 10 along the male threads 11. The linear movement of the nut 10 causes the linear movement of a linkage 29 pivoted to the nut 10. This linear movement of the linkage 29 causes the linear movement of the stopper pin 14 equipped on the linkage 29. Moreover, the stopper pin 14 makes engagement with the curved slit 15 in the joint 2 of the opposed rotating outer shell 1 and, therefore, moves under guidance of slit 15 to move back-and-forth rotary the joint 2, so that the joint 2 makes angular movement around the pin 24 to get the outer shell 1 rotating, thereby bending the outer shell 1. The outer shells 1A~1D, as respectively connected to the power transmission shaft 5A~5D through a combination of the nut 10 and the male threads, are allowed to make bending movement independently from each other.

With the multi-articulated manipulator of the present invention, the joint members 3 are composed of the first joint member 3A to move the grasping member 4 with respect to the outer shell 1 in a vertical direction, the second joint 3B to move the outer shell 1A with respect to the outer shell 1B in horizontal direction perpendicular to the vertical direction, the third joint 3C to move the outer shell 1B with respect to the outer shell 1D in a vertical direction and fourth joint 3D to move the outer shell 1C relative to the outer shell 1D.

Figure 4:
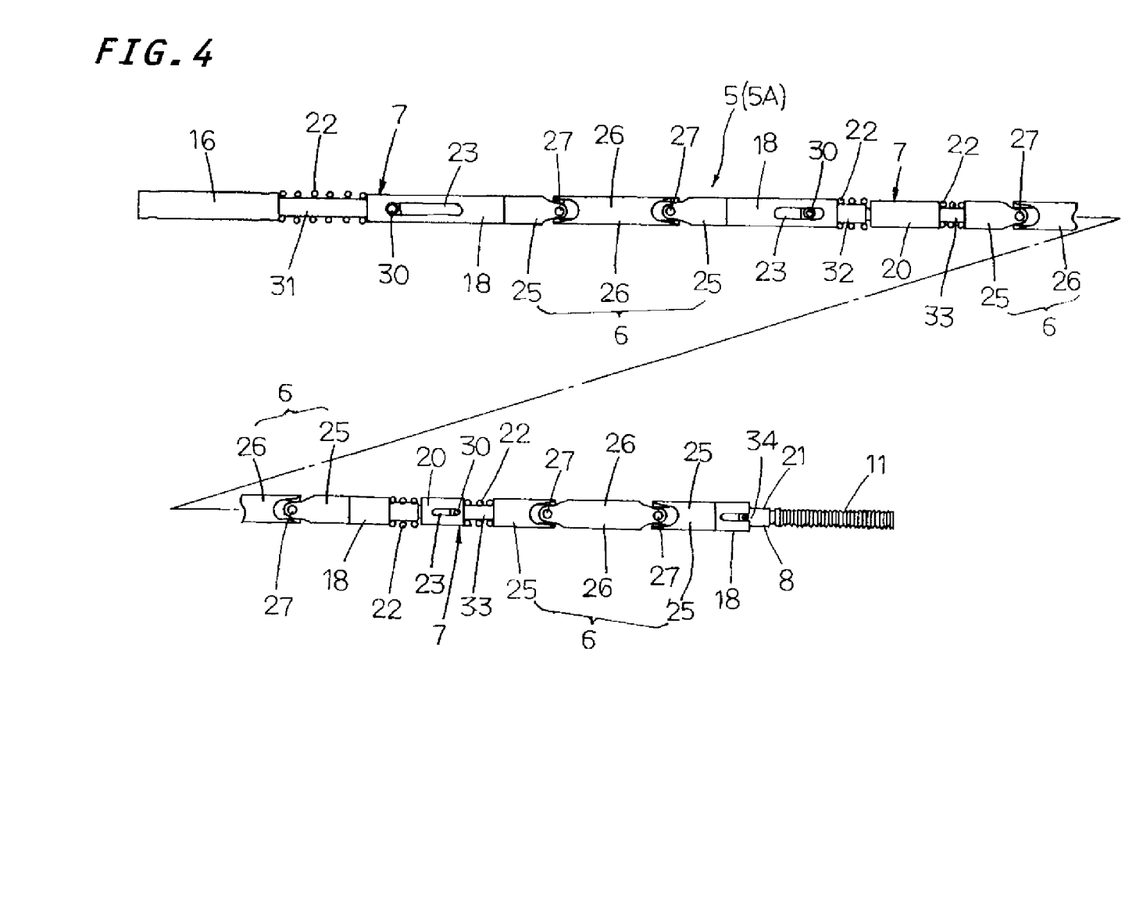
FIG. 4 is an enlarged plan view showing a most elongated power transmission shaft incorporated in the multi-articulated manipulator and connected with an outer shell lying at the foremost end thereof to operate the grasping members.
Figure 5:
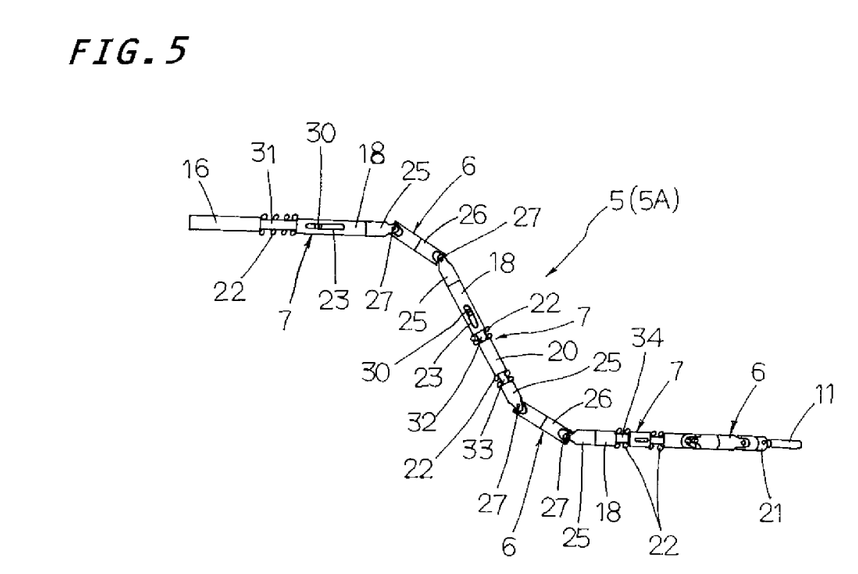
FIG. 5 is a scale-down plan view showing the power transmission shaft of FIG. 4 in a folded phase.
Figure 6:
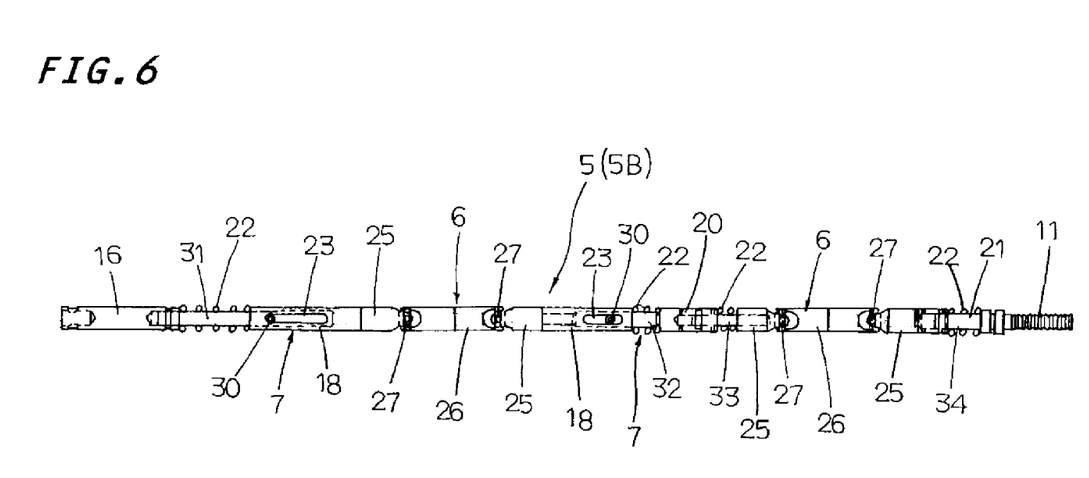
FIG. 6 is a plan view showing the power transmission shaft incorporated in the multi-articulated manipulator to operate an outer shell lying at the foremost end thereof.

With the transmission shaft 7 in the power transmission shaft 5, the first power transmission shaft 5A and the second power transmission shaft 5B extend long in lengthwise direction and have a second folder 20 at the transmission shaft 7, whereas the third power transmission shaft 5C and the forth power transmission shaft 5D are short in lengthwise direction, but have no second folder 20 at the transmission shaft 7. First, the power transmission shaft 5 having the folder 20 at the transmission shaft 7 will be explained below. The transmission shaft 7 is composed of an operating shaft 16 lying at base end and having a first shaft part 31, a first folder 18 fitting over the first shaft part 31 in a sliding manner and having fastened to a universal joint 6, a folder 20 having a second shaft part 32 fit into the first folder 18 for sliding movement, a universal joint 6 having a third shaft part 33 fit into the folder 20 for sliding movement, a driving shaft 21 formed with a male threads and having a fourth shaft part 34 which fits for sliding movement into the first folder 18 fastened to the foremost universal joint 6 and springs 22 installed between the operating shaft 16 and the folder 18, the folder 18 and the folder 20, the folder 20 and the universal joint 6, and the folder 18 and the driving shaft 21 (refer to FIGS. 4 to 6). Moreover, the shaft parts 31 to 34 have radially extended pins 30. The folders 18 and 20 have slits 23 which extended lengthwise of the folders. The pins 30 fit into the slits 23 to be guided along the slits 23. The shaft parts 31 to 34 are guided lengthwise but kept against rotation.

Figure 7:
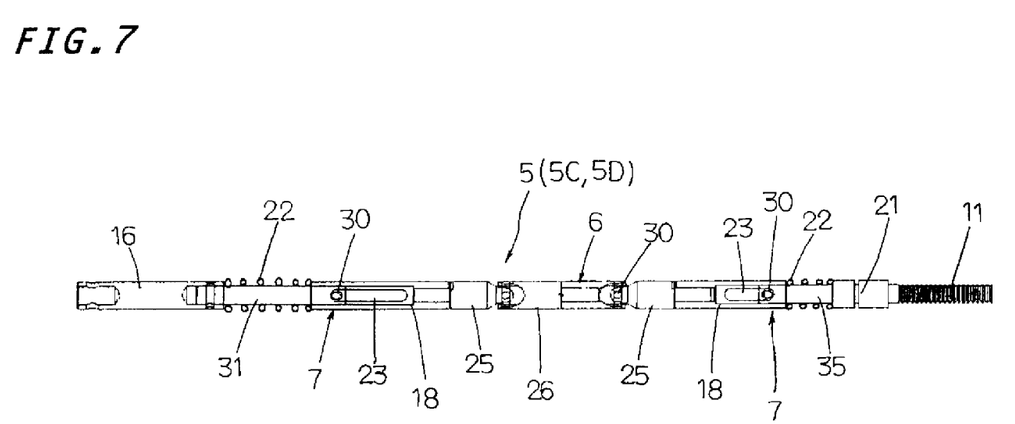
FIG. 7 is a plan view showing the power transmission shaft incorporated in the multi-articulated manipulator to operate an outer shell lying at the basement.
Figure 8:
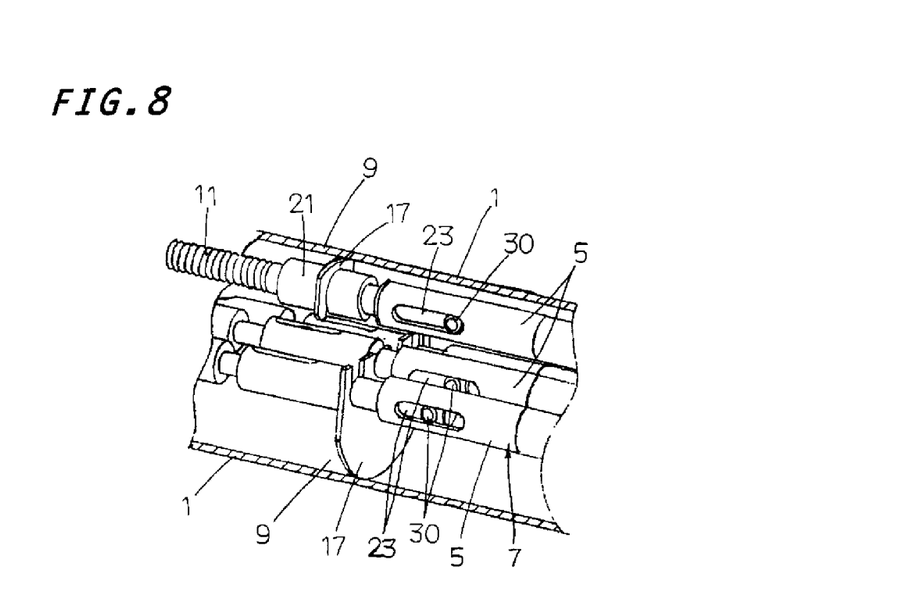
FIG. 8 is a perspective view showing a phase in which a thin plate is fastened to an outer shell to restrict elongation and shrinkage of the power transmission shaft.

Next refer to FIG. 7, the power transmission shaft 5 having no folder 20 will be explained below. The transmission shaft 7 is composed of an operating shaft 16 lying at base end and having a first shaft part 31, a folder 18 fitting over the first shaft part 31 in a sliding manner and having fastened to a universal joint 6, a driving shaft 21 having a fifth shaft part 35 which fit for sliding movement into the first folder 18 fastened to the foremost universal joint 6 for sliding movement, a universal joint 6 having the third shaft part 33 fit into the folder 20 for sliding movement, the driving shaft 21 formed with a male threads 11 and having the fourth shaft part 35 which fits for sliding movement into the folder 18 fastened to the foremost universal joint 6 and the springs 22 installed between the operating shaft 16 and the folder 18, the folder 18 and the driving shaft 21. The shaft parts 31 to 35 are fastened radially with the pin 30. The folder 18 has the slit 23. Like with the above, the pin 30 fits into the slit 23 to be guided along the slit 23. Thus, the shaft parts 31 and 34 are constructed to keep the folder 18 against rotation and guide the folder 18 lengthwise.

The power transmission shaft 5 is composed of a pair of power transmission shafts 5A to actuate the grasping member 4 in a vertical direction, a pair of power transmission shafts 5B to actuate the outer shell 1A relative to the outer shell 1B in a horizontal direction, a single power transmission shaft 5C to actuate the outer shell 1B with respect to the outer shell 1C in a vertical direction, and a single power transmission shaft 5D to actuate the outer shell C with respect to the outer shell 1D in a vertical direction. Thus, the power transmission shaft 5 is composed of six shafts in all, namely, two power transmission shafts 5A, two power transmission shafts 5B, a single power transmission shaft 5C and a single power transmission shaft 5D. The power transmission 5 is inserted in the outer shell 1 and the joints 2. More particularly, two power transmission shafts 5A are inserted in the outer shell 1A. Two power transmission shafts 5A and two power transmission shafts 5B are accommodated in the outer shell 1B. Two power transmission shafts 5A, two power transmission shafts 5B and single power transmission shaft 5C are received in the outer shell 1C. Moreover, two power transmission shafts 5A, two power transmission shafts 5B, single power transmission shaft 5C and single power transmission shaft 5D are received in the outer shell 1D.

The universal joint 6 in the power transmission shaft 5 is a universal coupling joint which is composed of a pair of lengthwise opposed end yokes 25, and a middle yoke 26 coupled at the opposite ends thereof with the end yokes 25 by means of joint pins 27. With the embodiment of the universal joint 6 described here, the end yokes 25 and the middle yoke 26 are coupled with the cross-shaped universal joints. Thanks to the cross-shaped joint pins 27, the universal joint 6 is allowed to transmit the power while turning as a whole. With the outer shell 1, the thin plate 17 fastened to the slit inside the boss portion 9 makes engagement with the transmission shaft 7 of the power transmission shaft 5 to limit the expansion/shrinkage range of the power transmission shaft 7. The grasping member 4 is supported by means of the pin 24 for revolving movement to the joint 2 which is fastened to an end of the outer shell 1A. The grasping member 4 as shown in FIGS. 1 and 2 is composed of a pair of fingers 4A, which are pivoted each other with a pin 28 to make swinging movement, so that the fingers 4A are actuated with two power transmission shafts 5A to make the vertical swinging movement each other to open/close the fingers 4A. The fingers 4A are allowed to open or spaced away from each other across 120 degrees.

Figure 11:
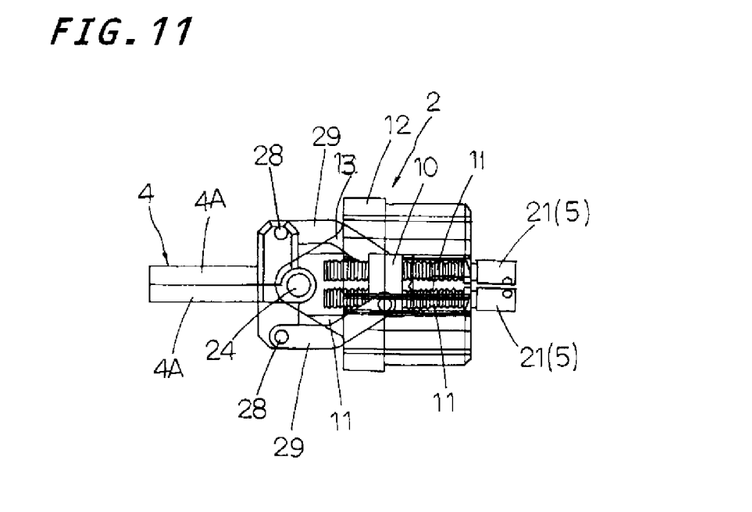
FIG. 11 is a plan view showing the grasping members connected with the power transmission shaft in the multi-articulated manipulator of the present invention.
Figure 12:
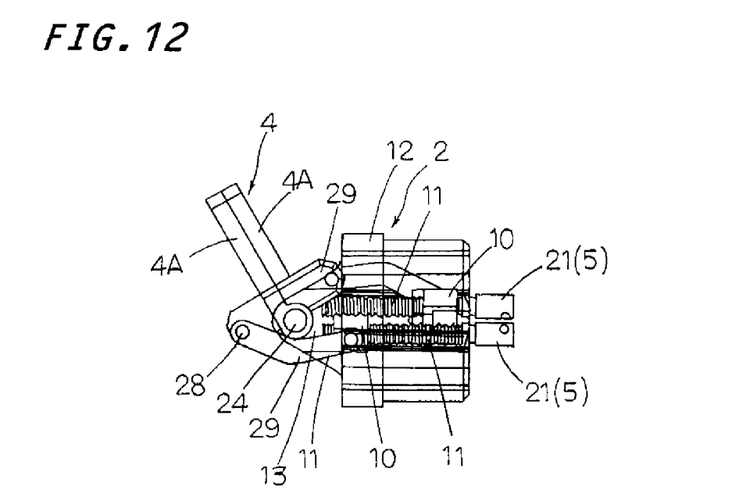
FIG. 12 is a plan view showing a phase in which the grasping members connected with the power transmission shaft in the multi-articulated manipulator of the present invention.

Next refer to FIGS. 11 and 12, operation of grasping members 4 will be described in detail. In FIG. 11, the power transmission shaft 5A isn't actuated and, therefore, the grasping fingers 4A of the grasping member 4 stays at their home phase. In FIG. 12, the grasping fingers 4A of the grasping member 4 are shown tilt or bent to any one direction by actuation of the driving shafts 21. When only the lower grasping finger 4A is actuated in opposed direction while the upper grasping member is left intact, the grasping fingers 4A separate away from each other. With the manipulator of multi-articulated construction of the present invention, thus, the grasping member 4 are allowed to vary their attitude while grasping fingers 4A stay just as they are intact. Moreover, the grasping member 4 may respond various requirements of bending and movements.

The multi-articulated manipulator constructed as stated earlier will be operated as follows. When the multi-articulated manipulator is intended to make the outer shell 1A bend the outer shell 1A from side to side with respect to the outer shell 1B as shown in FIG. 2, two power transmission shafts 5B are actuated to turn the male threads 11 to move linearly the nut 10 to actuate the linkage 29, thereby getting the outer shell 1A bending from side to side relatively to the outer shell 1B. Upon upward bending of the outer shell 1B with respect to the outer shell 1C, one of the power transmission shafts 5C is actuated likewise with the above to turn the male threads 11 to move linearly the nut 10 to actuate the linkage 29, thereby getting the outer shell 1B bending upwards relatively to the outer shell 1C. Upon downward bending of the outer shell 1C with respect to the outer shell 1D, moreover, only one power transmission shafts 5D is actuated to turn the male threads 11 to move linearly the nut 10 to actuate the linkage 29, thereby getting the outer shell 1C bending downwards relatively to the outer shell 1D. Upon actuation of the grasping fingers 4A of the grasping member 4, moreover, two power transmission shafts 5A are actuated to turn the male threads 11 to move linearly the nut 10 to actuate the linkage 29, thereby opening and closing each other the paired grasping fingers 4A. In FIG. 2, one of the grasping fingers 4A are shown bent downwards.

Figure 9:
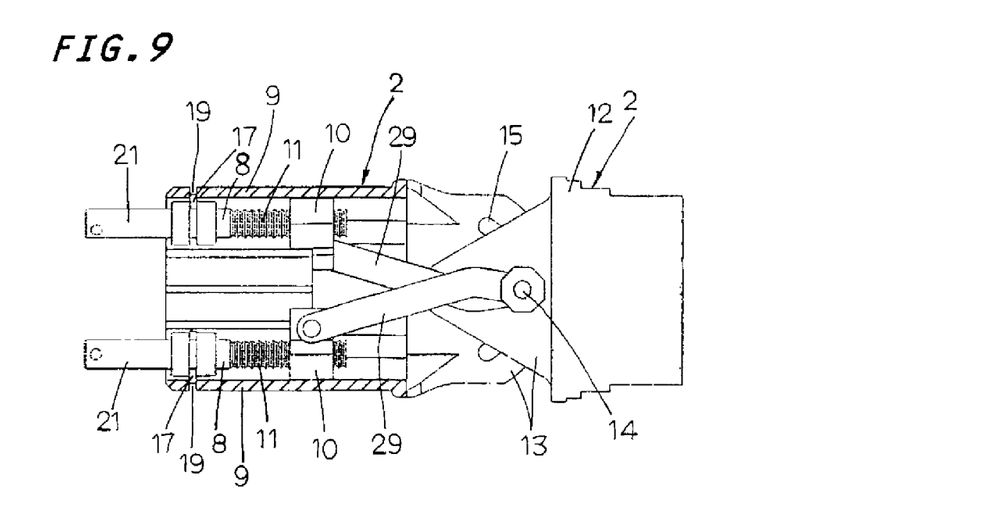
FIG. 9 is an explanatory view illustrating the power transmission shaft gets the outer shell bending in the multi-articulated manipulator of the present invention.
Figure 10:
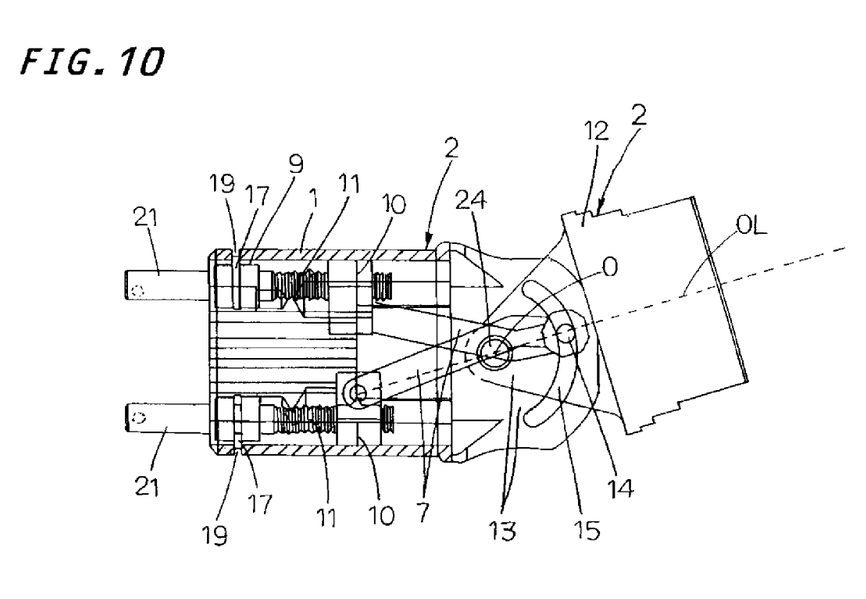
FIG. 10 is an explanatory view illustrating a phase the power transmission shaft gets the outer shell bending in the multi-articulated manipulator of FIG. 9.

The following with reference to FIGS. 9 and 10 describes the procedure to actuate the pair of power transmission shafts 5 to bend the joint members 3 thereby bending the outer shell 1 in the multi-articulated manipulator.

In FIG. 9, there is shown a phase in which, upon actuation of the pair of power transmission shafts, the foremost outer shell 1A is bent with the joint members 3B. The joint members 3B are in straight condition so that the foremost outer shell 1A and the second outer shell 1B extend in linear relation each other. Upon bending upwards the outer shell 1A relatively to the second outer shell 1B at the joint 2 in FIG. 9, the male threads 11 at the foremost end 8 of the upper power transmission shaft 5B of the power transmission shaft 5 is actuated for rotation to pull the nut 10 of the boss portion 9 in the outer shell 1B and at the same time, the male threads 11 at the foremost end 8 of the lower power transmission shaft 5B is actuated for rotation to pull the nut 10 of the boss portion 9 in the outer shell 1A. On the other hand, one end of the linkage 29 is pivoted to the nut 10 and the other end of the linkage 29 is pivoted to the nut 10 is pivoted to the stopper pin 14 which is guided with the curved slit 15 in the joint 2 of the outer shell 1B. The stopper pin 14 is made on the joint 2 of the opposing outer shell 1B. Thus, when the upper power transmission shaft 5B is pulled and the lower power transmission shaft 5B is pushed, the stopper pin 14 because made on the joint 2 of opposing outer shell 1B pulls the upper power transmission shaft 5B. On the other hand, the stopper pin 14 when the lower power transmission shaft 5B is pushed gets to tilt the outer shell 1A upwards relative to the outer shell 1B around the pin 24 (refer to FIG. 10). The movement as described above is carried out until the linkage 29 reaches the center axis OL or the rotational center 0 of the pin 24, namely inflection point and gets reversed the condition pushing the lower power transmission shaft 5B to pulling condition (not shown). Thus, after the power transmission shaft 5B is operated to pull the outer shell 1A towards the outer shell 1B until the outer shell 1A at maximum the stopper pin 14 reaches the upper end of the slit 15, the outer shell 1B tilts upwards at the maximum with respect to the outer shell 1A. In order to return the outer shell 1A to the original linear relation with the outer shell 1B, it is sufficient to reverse the operation described above to actuate the upper and lower power transmission shafts 5.

Next, in order to tilt downwards the outer shell 1B with respect to the outer shell 1A, it is sufficient to actuate the upper and lower power transmission shafts 5 in opposite directions. Namely, the upper second power transmission shafts 5B is pushed forwards and the lower second power transmission shafts 5B is retracted to move downwards the stopper pin 14 along the slit 15. After the stopper pin 14 on the linkage 29 has reached the inflection point lying on the rotational center of the pin 24, the lower second power transmission shaft 5B continues retracted, but the upper second power transmission shaft 5B is driven reversely to be retracted. Then, the second power transmission shaft 5B is actuated to pull the outer shell 1A towards the outer shell 1B. After the stopper pin 14 has reached the lower end of the slit 15, the outer shell 1A is tilted at maximum downwards relative to the outer shell 1A. Next, in order to return the outer shells 1A and 1B to the original linear situation, it is sufficient to operate the upper and lower power transmission shafts 5 in reverse against operations as stated just earlier.

What is claimed is:

1. A multi-articulated manipulator comprising:
more than one hollow outer shells lying lengthwise, a joint fastened to opposite ends of the outer shells, a joint member to connect joints opposed to each other, a grasping member connected for rotation to the joint members opposed each other, and more than one power transmission shafts which fits into the outer shells and the joint for expansion and shrinkage and further bending to operate the grasping member and the outer shells independently from each other in a bending manner, wherein the power transmission shafts each have a plurality of transmission shafts capable of extension and shrinkage and transferring a rotating torque, and more than one universal joints capable of bending to connect the adjacent transmission shafts each other and transmit the rotating torque, wherein the power transmission shafts have second threaded portions which are allowed to mate into first threaded portions made in boss portions in the outer shells, wherein the outer shells are composed of a first outer shell lying at a foremost end of the outer shells, a second outer shell adjacent to the first outer shell, a third outer shell adjacent to the second outer shell, and a fourth outer shell adjacent to the third outer shell, wherein the power transmission shafts are composed of a pair of first power transmission shafts to actuate the grasping member with respect to the first outer shell in a vertical direction, a pair of second power transmission shafts to actuate the first outer shell relative to the second outer shell in a horizontal direction perpendicular to the vertical direction, a single third power transmission shaft to actuate the second outer shell with respect to the third outer shell in a vertical direction, and a single fourth power transmission shaft to actuate the third outer shell with respect to the fourth outer shell in a vertical direction, and wherein the transmission shafts of the power transmission shafts are composed of operating shafts lying at base end and having a first shaft part, a first folder fitting over the first shaft part in a sliding manner and having fastened to a universal joint, a second folder having a second shaft fit into the first folder for sliding movement, a universal joint having a third shaft fit into the second folder for sliding movement, a driving shaft formed with a male threads and having a fourth shaft which fits for sliding movement into the first folder fastened to the foremost universal joint, and springs installed between the first folder and the operating shaft, and the first folder and the second folder, the second folder and the universal joint, and the first folder and the driving shaft, and wherein pins are diametrically fastened to the first, second, third and fourth shaft parts to fit into slits in the first folder and the second folder to be guided in a lengthwise direction, but kept against rotation.

2. The multi-articulated manipulator defined in claim 1, wherein the joint member each fastened to one of opposite ends of the outer shells are composed of a circular part fastened to the outer shell, and a pair of raised portions or U-shaped raised portions extended integrally from circumferentially opposite locations of the circular part.

3. The multi-articulated manipulator defined in claim 1, wherein the joint fastened to one of the opposite ends of the outer shells have a stopper pin extended outwardly and another joint fastened to another of the opposite ends of the outer shell has a curved slit, and further the stopper pin made on the joint makes engagement with the curved slit in the adjacent joint to limit a bending range between adjacent joint members.

4. The multi-articulated manipulator defined in claim 1, wherein the first threaded portion on the boss portion of the outer shell is a nut and the second threaded portion on the transmission shafts are male threads mating with the nut.

5. The multi-articulated manipulator defined in claim 1, wherein the joint is composed of a first joint member to move the grasping member with respect to the outer shell in a vertical direction, a second joint to move the outer shell with respect to the second outer shell in a horizontal direction perpendicular to the vertical direction, a third joint to move the second outer shell with respect to the third shell in a vertical direction and a fourth joint to move the third outer shell relative to the fourth outer shell.

6. The multi-articulated manipulator defined in claim 1, wherein the universal joint in the power transmission shafts are composed of a pair of lengthwise opposed end yokes, and a middle yoke coupled at the opposite ends thereof with the end yokes by means of joint pins using the cross-shaped universal joints.

7. The multi-articulated manipulator defined in claim 1, wherein a thin plate fastened inside the outer shell makes engagement with the transmission shaft parts of the power transmission shafts to restrict an expansion/shrinkage range of the power transmission shaft.

8. The multi-articulated manipulator defined in claim 1, wherein the grasping member is composed of a pair of fingers which are supported for swinging movement with respect to each other with connecting pins fastened to the end of the first outer shell, so that the fingers are operated by the two first power transmission shafts to grasp an object.

9. The multi-articulated manipulator defined in claim 1, wherein the outer shells, the joint members and the transmission shafts are made of metallic material rich in rigidity or stiffness.

10. A multi-articulated manipulator comprising:
more than one hollow outer shells lying lengthwise, a joint fastened to opposite ends of the outer shells, a joint member to connect joints opposed to each other, a grasping member connected for rotation to the joint members opposed each other, and more than one power transmission shafts which fits into the outer shells and the joint for expansion and shrinkage and further bending to operate the grasping member and the outer shells independently from each other in a bending manner, wherein the power transmission shafts each have a plurality of transmission shafts capable of extension and shrinkage and transferring a rotating torque, and more than one universal joints capable of bending to connect the adjacent transmission shafts each other and transmit the rotating torque,
wherein the power transmission shafts have second threaded portions which are allowed to mate into first threaded portions made in boss portions in the outer shells,
wherein the outer shells are composed of a first outer shell lying at a foremost end of the outer shells, a second outer shell adjacent to the first outer shell, a third outer shell adjacent to the second outer shell, and a fourth outer shell adjacent to the third outer shell,
wherein the power transmission shafts are composed of a pair of first power transmission shafts to actuate the grasping member with respect to the first outer shell in a vertical direction, a pair of second power transmission shafts to actuate the first outer shell relative to the second outer shell in a horizontal direction perpendicular to the vertical direction, a single third power transmission shaft to actuate the second outer shell with respect to the third outer shell in a vertical direction, and a single fourth power transmission shaft to actuate the third outer shell with respect to the fourth outer shell in a vertical direction, and
wherein the transmission shafts of the power transmission shafts are composed of operating shafts lying at base end and having a first shaft part, a first folder fitting over the first shaft part in a sliding manner and having fastened to a universal joint, a driving shaft formed with a second threads and having a fifth shaft part which fits for sliding movement into the first folder fastened to the foremost universal joint, and springs installed between the operating shaft and the first folder, and the first folder and the driving shaft, and pins fastened diametrically to the first shaft part and the fifth shaft part so as to fit into the slits in the first folder, thereby being guided lengthwise with no rotation.

11. The multi-articulated manipulator defined in claim 10, wherein the joint member each fastened to one of opposite ends of the outer shells are composed of a circular part fastened to the outer shell, and a pair of raised portions or U-shaped raised portions extended integrally from circumferentially opposite locations of the circular part.

12. The multi-articulated manipulator defined in claim 10, wherein the joint fastened to one of the opposite ends of the outer shells have a stopper pin extended outwardly and another joint fastened to another of the opposite ends of the outer shell has a curved slit, and further the stopper pin made on the joint makes engagement with the curved slit in the adjacent joint to limit a bending range between adjacent joint members.

13. The multi-articulated manipulator defined in claim 10, wherein the first threaded portion on the boss portion of the outer shell is a nut and the second threaded portion on the transmission shafts are male threads mating with the nut.

14. The multi-articulated manipulator defined in claim 10, wherein the universal joint in the power transmission shafts are composed of a pair of lengthwise opposed end yokes, and a middle yoke coupled at the opposite ends thereof with the end yokes by means of joint pins using the cross-shaped universal joints.

15. The multi-articulated manipulator defined in claim 10, wherein a thin plate fastened inside the outer shell makes engagement with the transmission shaft parts of the power transmission shafts to restrict an expansion/shrinkage range of the power transmission shaft.

16. The multi-articulated manipulator defined in claim 10, wherein the outer shells, the joint members and the transmission shafts are made of metallic material rich in rigidity or stiffness.

\* \* \* \* \*